(12) United States Patent
Starling et al.

(10) Patent No.: US 7,112,304 B2
(45) Date of Patent: Sep. 26, 2006

(54) ROBUST CHEMIRESISTOR SENSOR

(75) Inventors: Jared Starling, Mansfield, OH (US); Prasad S. Khadkikar, Lexington, OH (US); Robert Sterken, Mansfield, OH (US); Charles L. Volz, Mansfield, OH (US); Edward J. Blok, Wadsworth, OH (US); Donald E. Donnelly, Fenton, MO (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 146 days.

(21) Appl. No.: 10/412,602

(22) Filed: Apr. 11, 2003

(65) Prior Publication Data
US 2004/0200722 A1 Oct. 14, 2004

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. ............ 422/83; 422/50; 422/56; 422/57; 422/58; 422/68.1; 422/69; 422/82.01; 422/82.02; 422/82.03; 422/82.04; 422/88; 422/97; 422/98; 73/1.01; 73/1.02; 73/23.2; 73/53.01; 438/14; 438/17; 438/48; 438/49; 29/25.01; 29/592; 29/592.1

(58) Field of Classification Search ............ 422/50, 422/56, 57, 58, 68.1, 69, 82.01, 82.02, 82.03, 422/82.04, 83, 88, 97, 98; 73/1.01, 1.02, 73/23.2, 53.01; 438/14, 17, 48, 49; 29/25.01, 29/592, 592.1

See application file for complete search history.

(56) References Cited

U.S. PATENT DOCUMENTS

| 2,740,032 A | 3/1956 | Bouyoucos |
| 3,705,375 A | 12/1972 | Hershler |
| 3,815,114 A * | 6/1974 | Johnson et al. ............ 422/95 |
| 3,848,218 A | 11/1974 | Wakabayashi et al. |
| 3,891,958 A | 6/1975 | Wakabayashi |
| 3,983,527 A | 9/1976 | Ohsato et al. |

(Continued)

FOREIGN PATENT DOCUMENTS

WO  WO 00/16081  3/2000

OTHER PUBLICATIONS

Communication from European Patent Office dated Nov. 10, 2004.

(Continued)

*Primary Examiner*—Jill Warden
*Assistant Examiner*—Brian Sines
(74) *Attorney, Agent, or Firm*—Harness, Dickey & Pierce, PLC

(57) ABSTRACT

A chemiresistor sensor probe for detecting target analytes. The probe includes a body having a first control surface and a second control surface recessed within the first. A sensor film comprises numerous conductive particles disposed upon the second surface. The film swells upon absorbing one or more analytes for which it has an affinity, thus causing the conductive particles to become more dispersed and increasing the resistance between the particles. The thickness of the film is equal to the distance between the first surface and the second surface, thus permitting the thickness to be controlled by varying the distance between the control surfaces. The robustness of the sensor probe is enhanced by placing a porous or mesh electrode along with, or in place of, a chemical binding agent between the film and the terminals. The robustness is also improved by placing a diode in series with the sensor circuit.

39 Claims, 3 Drawing Sheets

U.S. PATENT DOCUMENTS

| | | | |
|---|---|---|---|
| 4,314,231 A * | 2/1982 | Walty | 338/328 |
| 4,399,424 A | 8/1983 | Rigby | |
| 4,413,502 A | 11/1983 | Ohta et al. | |
| 4,423,407 A | 12/1983 | Zuckerman | |
| 4,450,428 A | 5/1984 | Ohta et al. | |
| 4,578,172 A | 3/1986 | Yamada et al. | |
| 4,580,439 A | 4/1986 | Manaka | |
| 4,631,952 A | 12/1986 | Donaghey | |
| 4,688,015 A | 8/1987 | Kojima et al. | |
| 4,707,244 A | 11/1987 | Harman, III et al. | |
| 4,713,646 A | 12/1987 | Sunano et al. | |
| 4,992,244 A * | 2/1991 | Grate | 422/98 |
| 5,004,700 A | 4/1991 | Webb et al. | |
| 5,006,828 A | 4/1991 | Yutaka et al. | |
| 5,071,626 A | 12/1991 | Tuller | |
| 5,075,667 A | 12/1991 | Nishiwaki et al. | |
| 5,086,286 A | 2/1992 | Yasukawa et al. | |
| 5,334,350 A | 8/1994 | Friese et al. | |
| 5,367,283 A | 11/1994 | Lauf et al. | |
| 5,476,003 A | 12/1995 | Neumann | |
| 5,506,569 A | 4/1996 | Rowlette | |
| 5,512,882 A * | 4/1996 | Stetter et al. | 340/632 |
| 5,605,612 A | 2/1997 | Park et al. | |
| 5,776,601 A | 7/1998 | Fournier et al. | |
| 5,777,207 A | 7/1998 | Yun et al. | |
| 6,161,421 A | 12/2000 | Fang et al. | |
| 6,221,673 B1 * | 4/2001 | Snow et al. | 436/149 |
| 6,325,979 B1 | 12/2001 | Hahn et al. | |
| 6,450,007 B1 | 9/2002 | O'Connor | |
| 6,495,892 B1 * | 12/2002 | Goodman et al. | 257/414 |
| 6,524,740 B1 * | 2/2003 | Broy et al. | 429/61 |

OTHER PUBLICATIONS

Eastman et al., "Application of the Solubility Parameter Concept to the Design of Chemiresistor Arrays", Journal of the Electrochemical Society, Jan. 20, 1999, pp. 3907-3913.

* cited by examiner

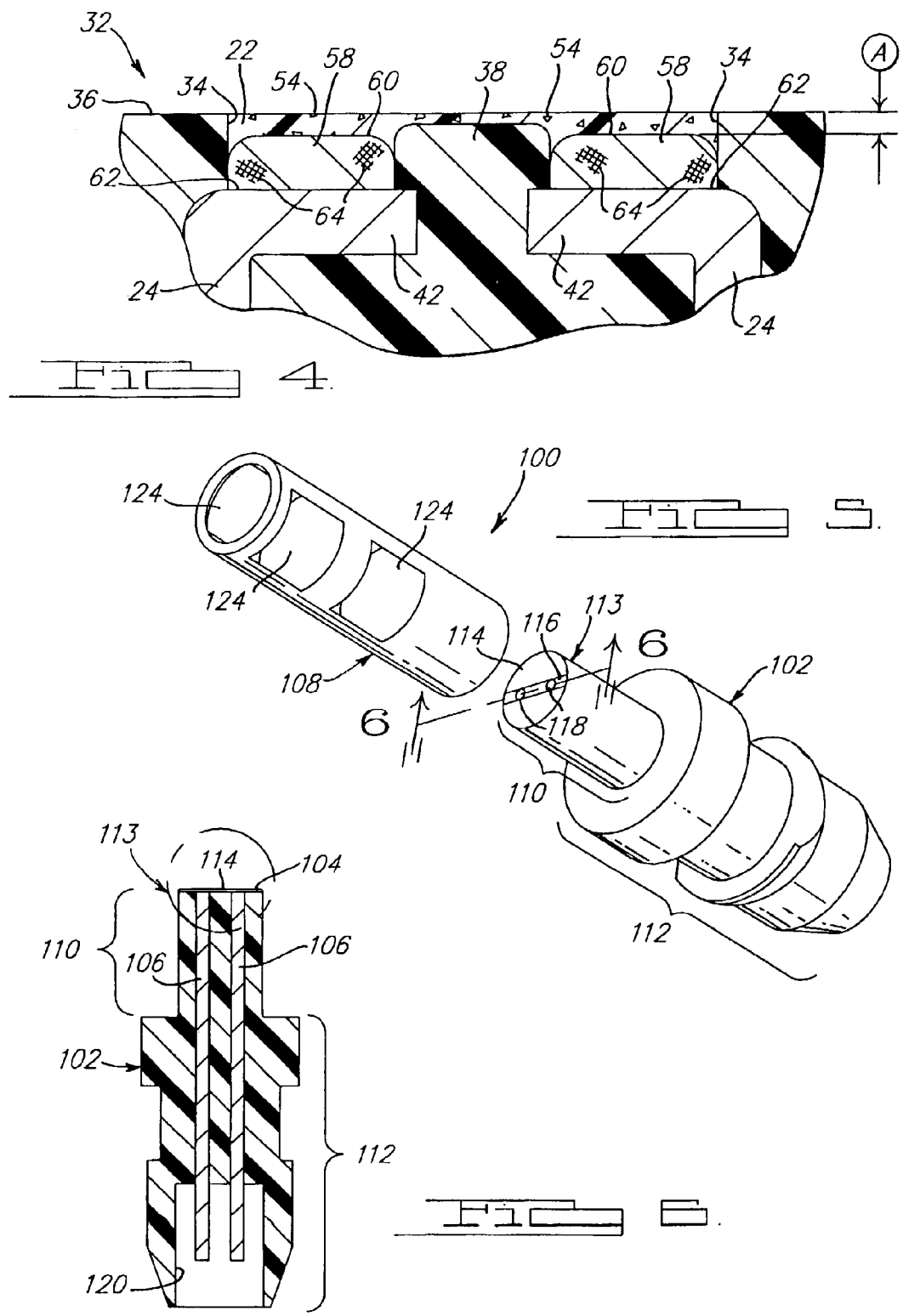

ROBUST CHEMIRESISTOR SENSOR

FIELD OF THE INVENTION

The present invention generally relates to chemiresistor sensors. In particular, the present invention relates to a chemiresistor sensor probe having a sensor film that detects target analytes.

BACKGROUND OF THE INVENTION

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe. Such processor is coupled to a user interface, typically containing an indicating device, which signals when concentration of an analyte has exceeded threshold values.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g. refractive index or color) in the film are monitored. Such changes in refractive index occur when analytes are absorbed and change the physical properties of the cladding (including volumetric changes). Other sensors include sound acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductiometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the electrical resistance of the film. Further, conductive particles may be distributed throughout the polymer film to enhance the sensitivity to resistance changes in the material when the volume of the polymer changes.

While conventional chemiresistor sensors perform adequately for their intended uses, they are subject to improvement. Specifically, as the volume of the sensor film expands and contracts over time in response to the presence of the target analytes, the mechanical bond between the sensor film and the terminals is weakened, thus causing the film to gradually separate from the terminals. As the film separates from the terminals the electrical bond between the film and the terminals is also weakened. This weakening of the electrical bond between the film and the terminals decreases sensor performance because it diminishes the ability of the processor to analyze changes in the resistance of the film through the terminals. Consequently, there exists a need for an improved chemiresistor that provides an enhanced mechanical and/or chemical bond between the terminals and the sensor film to enhance both the robustness of the sensor and the responsiveness of the sensor to the target analytes.

Conventional chemiresistor sensors are also deficient in that they fail to provide a sensor probe having a sensor film of a controlled thickness. The thickness of the sensor film is relevant to the probe's ability to detect the target analytes. Specifically, the use of a thick sensor film is undesirable because thick films require an extended period of time to absorb the target analyte, thus increasing the time required for the sensor film to swell and produce a change in resistance indicating the presence of the target analyte. However, the use of a sensor film that is overly thin is also not desirable because excessively thin films are not durable, are difficult to manufacture, and are unstable. Thus, there is also a need for a chemiresistor that has a sensor probe with a sensor film of a controlled thickness.

Additionally, a build-up of dirt or surface moisture may contaminate the terminals of conventional sensor probes, causing the sensor to produce inaccurate readings. Specifically, the surface moisture effectively creates a bypass resistor in parallel resistance with the sensor probe. This bypass resistor typically desensitizes the performance of the sensor. In particular, if the bypass resistance becomes small enough, the combined resistance of the bypass resistor in parallel with the sensor probe is influenced more by the bypass resistor, thus a very low level current will run into the sensor probe. Consequently, there is also a need for a chemiresistor sensor having a sensor probe with a circuit that is insensitive to bypass resistance.

SUMMARY OF THE INVENTION

The present invention improves upon the prior art by providing a chemiresistor sensor probe having a first control surface and a second control surface that permit control over the thickness of the sensor film. Recessed within the first control surface is the second control surface. The sensor film is disposed upon the second control surface and does not extend beyond the first control surface. The thickness of the sensor film is equal to the distance that the second control surface is recessed within the first control surface, thus permitting the thickness to be controlled by varying the distance that the second control surface is recessed within the first control surface.

The sensor probe of the present invention is also more robust than conventional probes. The probe of the present invention is made more robust due to an enhanced mechanical and/or chemical bond between the sensor film and terminals in electrical contact with the sensor film. The enhanced mechanical bond is preferably provided by a porous or mesh electrode placed between the sensor film and the terminals. The chemical bond may be provided by an appropriate chemical adhesive placed between the sensor film and the terminals. The electrode and/or the chemical adhesive also enhances the electrical connection between the sensor film and the terminals, thus increasing the responsiveness of the probe to the target analytes.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is an exploded view of a sensing region of the sensor probe of FIG. 3;

FIG. 5 is a perspective view of the chemiresistor sensor probe of FIG. 1 according to a second preferred embodiment of the present invention;

FIG. 6 is a cross-sectional side view of the sensor probe of FIG. 5 taken along line 6—6 of FIG. 5;

DETAILED DESCRIPTION OF THE PREFERRED EMBODIMENTS

The following description of the preferred embodiments is merely exemplary in nature and is in no way intended to limit the invention, its application, or uses.

Figure 1:
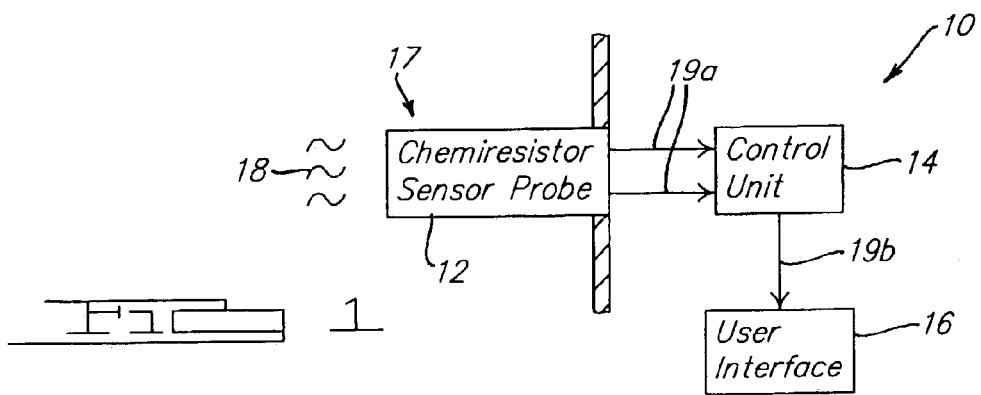
FIG. 1 is a block diagram of chemiresistor sensor operation according to a preferred embodiment of the present invention.

FIG. 1 generally depicts the major components of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The user interface 16 provides information to an external user about the sensor 10 and may range from a simple alarm signal to a complex computerized screen.

Figure 2:
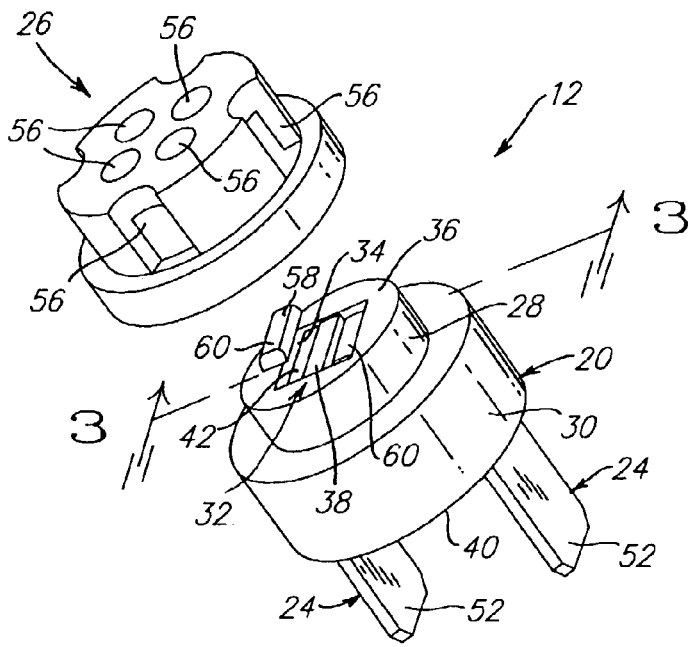
FIG. 2 is a perspective view of the chemiresistor sensor probe of FIG. 1 according to a first preferred embodiment.

FIG. 2 provides a detailed illustration of the sensor probe 12 according to a first preferred embodiment. The sensor probe 12 generally includes a probe body 20, a conductive sensor film 22 (FIGS. 3 and 4), a pair of terminals 24 extending from the probe body 20, and a protective cap 26.

The probe body 20 includes a first diameter portion 28 and a second diameter portion 30, the first diameter portion 28 having a diameter that is smaller than the second diameter portion 30. The first diameter portion 28 includes a sensing region 32. The sensing region 32 is comprised of two apertures 34 located within a first control surface 36. Between the apertures 34 is a second control surface 38. The second control surface 38 extends across the sensing region 32 and is slightly recessed within the first control surface 36.

The terminals 24 are embedded within the probe body 20 and extend from the apertures 34 through both the first diameter portion 28 and the second diameter portion 30. The terminals 24 protrude from the probe body 20 at an underside 40 of the second diameter portion 30. The terminals 24 are made of a conductive material, preferably a metal.

Figure 3:
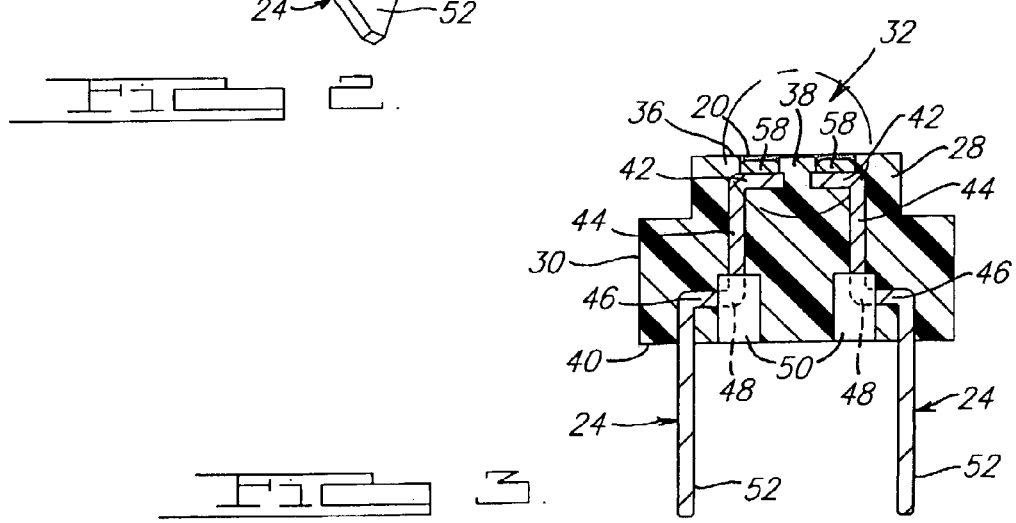
FIG. 3 is a cross-sectional side view of the sensor probe of FIG. 2 taken along line 3—3 of FIG. 2.

As seen in FIG. 3, the terminals 24 each comprise a first horizontal portion 42 that is parallel to the first control surface 36 and approximately equals the width of one of the apertures 34. Extending from the first horizontal portion 42 is a first vertical portion 44. The first vertical portion 44 extends through the first diameter portion 28 and into the second diameter portion 30 where the first vertical portion 44 transitions to a second horizontal portion 46.

At the transition point between the first vertical portion 44 and the second horizontal portion 46, the terminals 24 each have an opening 48. The opening 48 receives an alignment rod (not shown) during manufacturing to permit precise alignment of the terminals 24 within the probe body 20. The use of the alignment rod during the molding process results in the formation of a bore 50 within the underside 40 of the probe body 20. The process of manufacturing the probe body 20 is described in detail below.

From the second horizontal portion 46 extends a second vertical portion 52. The second vertical portion 52 extends from the underside 40 of the second diameter portion 30. The second vertical portion 52 extends from the probe body 20 to an appropriate length to permit receipt of the terminals 24 by a corresponding outlet (not shown) that is in communication with the control unit 14.

Illustrated most clearly in FIG. 4, the sensor film 22 is bonded or secured to the sensing region 32 in any suitable manner, such as by solution deposition, so that the sensor film 22 fills the apertures 34 and spans the second control surface 38. The film 22 fills the apertures 34 so that the film 22 is in electrical contact with both terminals 24 through either direct or indirect physical contact with the terminals 24. The film 22 is comprised of a plurality of conductive particles 54 positioned throughout the film 22. The film 22 is preferably a crosslinked, polymeric matrix, but may be any type of sensor film that absorbs one or more different analytes 18 of interest, such as liquids, vapors, or gases.

The sensing region 32 provides a control over the thickness of the sensor film 22. At its thinnest point, the film 22 is only as thick as the distance between the first control surface 36 and the second control surface 38, represented as distance A in FIG. 4. The thickness of the film 22 may be controlled by varying the distance (distance A) between the first control surface 36 and the second control surface 38. Distance A may be any appropriate distance but is preferably between two and three thousandths of an inch. To control the effective thickness of the film 22 it is significant to control the thickness at distance A because the effective thickness of the entire film 22 is primarily dependent upon the thickness of the film 22 at its thinnest point, which is at distance A.

The protective cap 26 may be any suitable cover capable of being inserted over the first diameter portion 28 of the probe body 20 to protect the sensing region 32 from being disturbed or damaged by foreign materials or objects. Additionally, the protective cap 26 must be capable of permitting the analytes 18 to pass through the cap 26 for absorption by the film 22. To permit passage of the target analyte 18 through the cap 26, the cap 26 is preferably outfitted with one or more pores or through bores 56. The cap 26 may be secured to the probe body 20 in any suitable manner but is preferably secured using a suitable adhesive.

The robustness of the probe 12 can be increased by providing a strong mechanical bond between the film 22 and the terminals 24. The mechanical bond is preferably provided by inserting a porous or mesh electrode 58 between the film 22 and the terminals 24. The electrode 58 may be made of any suitably conductive material but is preferably a metal. As seen in FIG. 4, the electrode 58 has an upper surface 60 and a lower surface 62. The upper surface 60 includes a porous or mesh surface 64. The lower surface 62 is in electrical and mechanical contact with the terminals 24 and is secured to the terminals 24 in any suitable manner, such as through sintering.

The upper surface 60 is in electrical and mechanical contact with the film 22. The porous or mesh surface 64 provides the upper surface 60 with a large porous or mesh surface area that the film 22 seeps within to interlock with the upper surface 60, thus providing a strong mechanical bond between the upper surface 60 and the film 22. Further, by increasing surface area of the connection between the upper surface 60 and the film 22 the porous or mesh surface 64 increases the number of bonds between the upper surface 60 and the film 22. The use of the electrode 58 extends the life of the sensor probe 12 by preventing the separation of the film 22 from the terminals 24 over time as the film 22 expands and contracts in response to the target analytes 18 being absorbed by the film 22.

The use of a chemical coupling agent between the terminals 24 and the film 22 also enhances the mechanical and electrical bonds between the film 22 and the terminals 24, thus providing a more robust sensor probe 12 and permitting the terminals 24 to detect changes in the resistance of the film 22 more precisely and more quickly. The coupling agent may be any appropriate adhesive capable of bonding the film 22 to the terminals 24 while permitting an electrical charge to pass between the terminals 24 and the film 22. Appropriate coupling agents include monoalkoxy titanate coupling agents, such as isopropyl tri-isostearoyl titanate, isopropyl tri(diocty)phosphate, and isopropyl (4-amino) benzenesulfonyl di(dodecyl) benzenesulfonyl titanate; chelate titanate coupling agents, such as di(dioctyl) pyrophosphate oxoethylene titanate, dimethyacryl oxoethylene, and di(dioctyl) pyrophosphate ethylene titanate; quat titanate and zirconate coupling agents, such as 2-n,N-dimethyl-amino isobutanol adduct of di(dioctyl)pyrophosphate oxoethylene titanate; coordinate titanate and zirconate coupling agents such as tetraisopropyl di(dioctyl) phosphito titanate, tetra (2,2 diallyoxymethyl) butyl, and di(ditridecyl)phosphito zirconate; neoalkoxy titanate coupling agents, such as neopentyl(diallyl)oxy, and tri(dioctyl)pyro-phosphato titanate; cycloheteroatom neoalkoxy titanate coupling agents, such as cyclo (dioctyl) pyrophosphato dioctyl titanate; neoalkoxy zirconate coupling agents, such as neopentyl (diallyl)oxy, tri(dioctyl)phosphato zirconate; aluminate coupling agents, such as diisobutyl (oleyl) acetyl aluminate and disopropyl (oleyl) aceto acetyl aluminate; and silane coupling agents, such as allyltriethoxysilane and dimethylethoxysilane.

Figure 7:
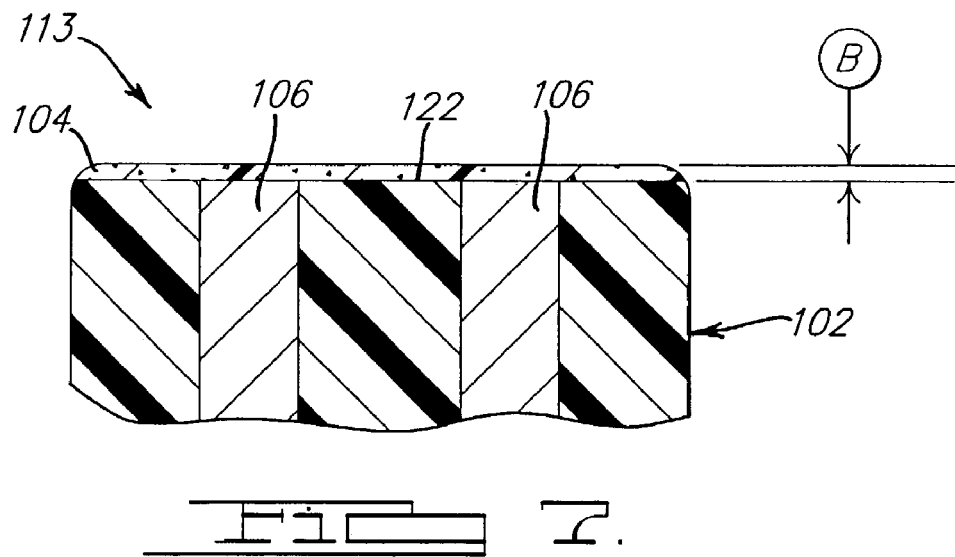
FIG. 7 is an exploded view of a sensing region of the sensor probe of FIG. 6.

An alternative preferred embodiment of the probe 12 is illustrated in FIGS. 5 through 7 at 100. Like the probe 12, the probe 100 generally includes a probe body 102, a sensor film 104 (FIGS. 6 and 7), a pair of terminals 106 (FIGS. 5 and 6), and a protective cap 108 (FIG. 5). The probe 100 is described in further detail below.

As seen in FIGS. 5 and 6, the probe body 102 includes a neck portion 110 and a base portion 112. The neck portion 110 includes a sensing region 113 having a first control surface 114. Recessed within the first control surface 114 is a second control surface 116. The second control surface 116 includes two apertures 118 through which the terminals 106 extend.

The terminals 106 extend from the apertures 118 through both the neck portion 110 and the base portion 112. The terminals 106 terminate in an interior cavity 120 (FIG. 6) of the base portion 112. The interior cavity 120 is sized such that it can receive a corresponding outlet (not shown) of the control unit 14, the outlet engaging the portions of the terminals 106 that extend within the cavity 120. The sensor film 104 is placed upon the second control surface 116 such that it spans the apertures 118 and makes electrical contact with the terminals 106, allowing the terminals 106 to detect changes in resistance between a plurality of conductive particles 122 of the sensor film 104.

The first control surface 114 and the second control surface 116 provide a control over the thickness of the sensor film 104. Specifically, the film 104 is initially applied over the second control surface 116 in excess such that the film 104 extends beyond the first control surface 114. The excess film 104 is subsequently removed so that the film 104 does not extend beyond the first control surface 114. Thus, the thickness of the film 104 is equal to the distance that the second control surface 116 is recessed within the first control surface 114, represented as distance B in FIG. 7. Distance B may be any suitable distance but is preferably between two and three thousandths of an inch.

The protective cap 108 may be any suitable cover capable of being inserted over the neck portion 110 to protect the first control surface 114 and the sensing film 22 from being disturbed or damaged by foreign materials or objects. Similar to the protective cap 26, the protective cap 108 includes one or more pores or through bores 124. The cap 108 may be secured to the sensor probe body 102 in any appropriate manner but is preferably secured using a suitable adhesive.

The robustness of the probe 100 can be enhanced by creating a strong mechanical bond between the sensor film 104 and the terminals 106. The mechanical bond is preferably provided by placing a porous or mesh electrode, such as the electrode 58 (FIG. 4), between the film 104 and the terminals 106. The film 104 seeps within the large porous or mesh surface area of the electrode to provide a great number of strong mechanical bonds between the electrode and the film 104. The electrode extends the life of the probe 100 by preventing the separation of the film 104 from the terminals 106 over time as the film 104 expands and contracts in response to the presence of the target analytes 18 being absorbed by the film 104.

In addition to, or in place of, the mechanical bond provided by placing the electrode between the terminals 106 and the sensor film 104, the robustness of the probe 100 may also be increased by inserting a chemical bond between the terminals 106 and the film 104. The chemical bond may be provided by any chemical coupling agent that is capable of bonding the film 104 to the terminals 106 while permitting an electrical charge to pass between the terminals 106 and the film 104. Chemical coupling agents that may be used include those listed above in the discussion relating to the sensor probe 12.

The manufacturing process of the probe body 20 will now be described in detail. As the manufacturing process of the probe body 20 is substantially similar to the manufacturing process of the probe body 102, the below description also applies to probe body 102. The probe body 20 is preferably manufactured using any appropriate plastic molding technique, such as insert molding. The molding process may be performed using any suitable molding compound, such as 30% glass reinforced polybutylene terephthalate, sold under the tradename VALOX420 by GE Plastics. The molding compound is dried and inserted into a mold that is prefabricated to produce a probe body 20 of a desired shape and size. The mold is specifically designed to produce a probe body 20 having the second control surface 38 slightly recessed below the first control surface 36. By varying the dimensions of the mold, the distance that the second control surface 38 is recessed within the first control surface 36 may be altered. As described above, the distance that the second control surface 38 is recessed within the first control surface 36 (distance A in FIG. 3) is equal to the thickness of the film 104 at its thinnest portion. Thus, by modifying the mold to produce probes 12 having second control surfaces 38 recessed within the first control surfaces 36 at different distances, the thickness of the film 22 may be controlled.

Before the molding compound is inserted into the mold, the terminals 24 are inserted into the mold such that when the molding compound is inserted and hardens, the terminals 24 are trapped within the probe body 20 and are molded in situ. To insure proper positioning of the terminals 24 within the probe body 20, the terminals 24 are each mounted within the mold upon separate rods (not shown) that are received by the opening 48 of the terminals 24. Because the terminals 24 are mounted upon the rods when the probe body 20 is molded around the terminals 24, the bores 50 are formed within the underside 40 of each probe body 20. Before the film 22 and the optional mechanical and chemical binding agents are applied to the terminals 24, the terminals 24 may be cleaned to enhance their performance.

After the probe body 20 is molded about the terminals 24, and the sensing region 32 is formed as a result of the molding process, optional mechanical binding agents, such as the porous or mesh electrodes 58, are inserted within each of the apertures 34 upon the second vertical portion 52 of the terminals 24. The porous or mesh electrodes 58 are secured to the terminals 24 in any suitable manner, such as through sintering or welding. Depending upon the depth of the apertures 34 and the thickness of the electrodes 58, it may be necessary to compress the electrodes 58 so that the electrodes 58 do not protrude beyond the first control surface 36 or the second control surface 38.

A chemical bond may also be created between the sensor film 22 and the terminals 24. The chemical bond may be used in addition to or in place of the mechanical bond. The chemical bond is provided by a chemical coupling agent placed between the film 22 and the terminals 24. The coupling agent may be any suitable coupling agent capable of creating a chemical bond between the film 22 and the terminals 24, such as the chemical coupling agents described above.

After the optional mechanical or chemical coupling agents are placed over the terminals 24, the sensor film 22 is applied over the first control surface 36 and the second control surface 38 in liquid or paste form. The film 22 is applied in excess such that it completely fills the apertures 34, spans the second control surface 38, and extends beyond the first control surface 36. Next, the excess sensor film 22 is removed so that the film 22 does not extend beyond the first control surface 36. The excess film 22 may be removed in any suitable manner, such as by running a razor blade over the first control surface 36.

After the film 22 is applied, the protective cap 26 is placed over the first diameter portion 28 and is secured to the probe body 20 in any suitable manner. After the film 22 is applied to the first control surface 36 and the second control surface 38, the film 22 is oven cured. The oven curing process is preferably performed at 120° C. for three hours.

The operation of the sensor probe 12 will now be described. The operation of the probe 100 is substantially similar to the operation of the probe 12 and thus the below description also applies to the operation of the probe 100. Upon exposure of the sensor probe 12 to one or more of the target analytes 18 within the external environment 17, the analytes 18 are absorbed by the film 22, causing the film 22 to swell. A mechanical bond, provided by the electrode 58, and/or a chemical bond located between the film 22 and the terminals 24 prevents the film 22 from becoming detached from the terminals 24 during the repeated swelling and contraction of the film 22, thus maintaining and enhancing the electrical connection between the film 22 and the terminals 24 to produce a more robust sensor probe 12.

As the film 22 swells, the distance between the conductive particles 54 increases, thus increasing the resistance of the film 22 as measured by the control unit 14 via both the terminals 106 and the raw output signal 19a. Upon detecting an increase in resistance between the terminals 24, the control unit 14 transmits a calculated output 19b to the user interface 16 instructing the user interface 16 to alert the user that the target analytes 18 have been detected by the probe 12. The user interface 16 may be any appropriate interface capable of providing an alert to the user. The interface 16 may range in complexity from a simple alarm to a complex computer providing audio and visual alerts.

Figure 8:
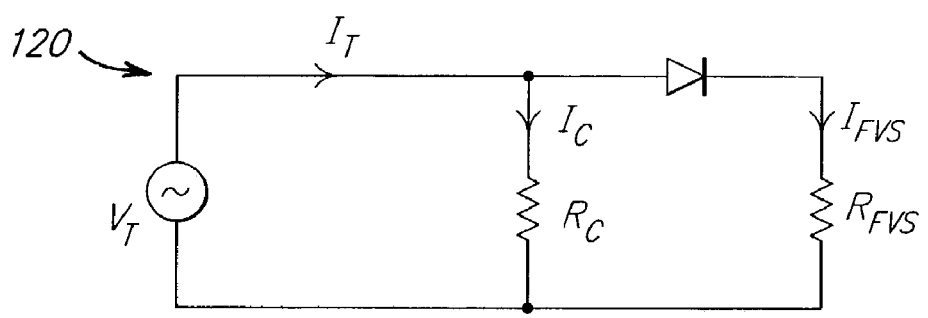
FIG. 8 is a sensor circuit according to a first embodiment for use with the chemiresistor circuit of the present invention.

FIG. 8, illustrates a typical sensor circuit 120 for use in the sensor 10. The circuit 120 comprises an AC voltage source $V_t$, a resistor $R_{fvs}$, a bypass resistor $R_c$, and a diode $D_1$ coupled in series with the resistor $R_{fvs}$. The resistor $R_{fvs}$ represents the resistance of the sensor probe 12 coupled in parallel to a bypass resistor $R_c$. The bypass resistor $R_c$ represents a build-up of dirt or surface moisture that may contaminate the probe 12. As is known, the AC voltage source $V_t$ comprises a positive and negative side of a sinusoid cycle.

In operation, the AC voltage source sends a current $I_t$, which is received by both the bypass resistor $R_c$ and resistor $R_{fvs}$. Specifically, a current $I_c$ flows through the bypass resistor $R_c$ and a current $I_{fvs}$ flows into both the diode $D_1$ and resistor $R_{fvs}$ in series. Thus, the total current of the circuit 120 equals the sum of the current $I_c$ and the current $I_{fvs}$. The current $I_{fvs}$ flowing into both the diode $D_1$ and the resistor $R_{fvs}$ is on the positive side of the sinusoid cycle from the AC voltage source $V_t$. The diode $D_1$ prevents the negative side of the AC cycle from going through the resistor $R_{fvs}$. The current $I_c$ flowing into the bypass resistor $R_c$ is received by both the positive and negative side of the sinusoid cycle. The total current on the positive side of the sinusoid cycle, $I_c+I_{fvs}$ is determined. The current on the negative side of the sinusoid cycle $I_c$ is also determined. Thus, current $I_t=I_c+(I_c+I_{fvs})$. As there are now two equations with two unknowns, the resistance values for resistors $R_{fvs}$ and $R_c$ can be determined using known mathematical formulas. It should be understood that the resistance values for resistor $R_{fvs}$ and $R_c$ can be determined through the control unit 14 or can be measured by well known measurement devices, such as, for example, a multi-meter.

The circuit 120 effectively takes into account the surface moisture that may contaminate the terminals 24 of the sensor probe 12, thus desensitizing the performance of the sensor 10. As such, the improved chemiresistor sensor 10 utilizing the circuit 120 provides accurate readings of the resistance of the sensor probe 12.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A chemiresistor sensor probe for detecting the presence of one or more target analytes in the atmosphere of an ambient environment, the probe comprising:

a body comprising a sensing portion and a terminal portion;

a sensor film located on said sensing portion; and first and second terminals disposed within said body, each of said first and second terminals extending from said sensing portion to the terminal portion and protruding from said body; and conductive interlocking portions, one each disposed between each of said first and second terminals and said sensor film, each said interlocking portion in direct contact with said sensor film and a respective one of said first and second terminals.

2. The chemiresistor sensor probe of claim 1, further comprising a cap attached to said body and covering said sensor film, said cap comprising at least one aperture that permits the atmosphere of the ambient environment to pass through the cap.

3. The chemiresistor sensor probe of claim 1, wherein at least one of said conductive interlocking portions comprise a conductive plate.

4. The chemiresistor sensor probe of claim 3, wherein said conductive plate comprises a mesh surface.

5. The chemiresistor sensor probe of claim 1, further comprising a chemical bond between at least one of said first and second terminals and said sensor film.

6. The chemiresistor sensor probe of claim 1, further comprising at least one aperture within each of said first and second terminals for receipt of a positioning rod for positioning said terminals within said body during manufacturing.

7. The chemiresistor sensor probe of claim 1, wherein said probe body comprises of a molded polymer.

8. The chemiresistor sensor probe of claim 1, wherein said sensor film comprises a crosslinked, polymeric matrix.

9. The chemiresistor sensor probe of claim 1, further comprising a sensor circuit having a diode to prevent bypass leakage from negatively affecting the performance of said sensor probe.

10. The chemiresistor sensor probe of claim 1, further comprising:

a plurality of conductive materials disposed within said sensor film, said conductive materials becoming more dispersed within said film as said film swells upon absorbing said analytes, thus increasing a resistance of said film.

11. The chemiresistor sensor probe of claim 1, wherein said sensor film is first applied to a second control surface of said sensing portion that is recessed beneath a first control surface in excess with a portion of said film extending beyond said first control surface being subsequently removed such that said film has a thickness equal to a distance that said second control surface is recessed beneath said first control surface.

12. The chemiresistor sensor probe of claim 1, further comprising:

a sensor circuit coupled with said sensor probe, said sensor circuit to prevent bypass leakage from negatively affecting performance of said sensor probe.

13. The chemiresistor sensor probe of claim 1, further comprising a control unit in communication with each of said first terminal and said second terminal to monitor electrical properties of said sensor film, said control unit is operable to generate a first signal representing the presence or absence of the analytes.

14. The chemiresistor sensor probe of claim 13, further comprising a user interface in communication with said control unit, said user interface operable to receive said first signal and generate a second signal representing the presence or absence of the analytes.

15. A chemiresistor sensor probe for detecting the presence of one or more target analytes in the atmosphere of an ambient environment, the probe comprising:

a molded body comprising a sensing region and a bottom surface opposite of said sensing region;

a sensor film comprising a cross-linked polymeric matrix located in said sensing region;

first and second terminals disposed within said body, each of said first and second terminals extending from said sensing region through said bottom surface so as to protrude from said body, each of said first and second terminals comprising an interlocking member disposed between and in direct contact with said sensor film and a respective one of said first and second terminals; and a molded cap attached to said body and covering said sensor film, said cap comprising at least one aperture which permits the atmosphere of the ambient environment to pass through the cap.

16. The chemiresistor sensor probe of claim 15, wherein at least one of said conductive interlocking members comprise a conductive plate.

17. The chemiresistor sensor probe of claim 16, wherein said conductive plate comprises a mesh surface.

18. The chemiresistor sensor probe of claim 15, further comprising a chemical bond between at least one of said first and second terminals and said sensor film.

19. The chemiresistor sensor probe of claim 15, wherein said sensor film is first applied to a second control surface of said sensing region that is recessed beneath a first control surface in excess with a portion of said film extending beyond said first control surface being subsequently removed such that said film has a thickness equal to a distance that said second control surface is recessed beneath said first control surface.

20. The chemiresistor sensor probe of claim 15, further comprising:

a sensor circuit coupled with said sensor probe, said sensor circuit to prevent bypass leakage from negatively affecting performance of said sensor probe.

21. The chemiresistor sensor probe of claim 15, further comprising a control unit in communication with each of said first terminal and said second terminal to monitor electrical properties of said sensor film, said control unit is operable to generate a first signal representing the presence or absence of the analytes.

22. The chemiresistor sensor probe of claim 21, further comprising a user interface in communication with said control unit, said user interface operable to receive said first signal and generate a second signal representing the presence or absence of the analytes.

23. A chemiresistor sensor probe for detecting the presence of one or more target analytes comprising:

a probe body;

a sensor film that absorbs the target analytes when the analytes are present mounted at an exterior surface of said probe body; and a first and a second terminal each having an interlocking device in direct contact with said sensor film.

24. The chemiresistor sensor probe of claim 23, further comprising a cap attached to said body and covering said sensor film, said cap comprising at least one aperture that permits the atmosphere of the ambient environment to pass through the cap.

25. The chemiresistor sensor probe of claim 23, wherein said interlocking device comprises a conductive plate.

26. The chemiresistor sensor probe of claim 25, wherein said conductive plate comprises a mesh surface.

27. The chemiresistor sensor probe of claim 23, further comprising a chemical bond between at least one of said first and second terminals and said sensor film.

28. The chemiresistor sensor probe of claim 23, wherein said probe body comprises a molded polymer.

29. The chemiresistor sensor probe of claim 23, wherein said sensor film comprises a crosslinked, polymeric matrix.

30. The chemiresistor sensor probe of claim 23, wherein said sensor film is first applied to a second control surface of said probe body that is recessed beneath a first control surface in excess with a portion of said film extending beyond said first control surface being subsequently removed such that said film has a thickness equal to a distance that said second control surface is recessed beneath said first control surface.

31. The chemiresistor sensor probe of claim 23, further comprising a control unit in communication with each of said first terminal and said second terminal to monitor electrical properties of said sensor film, said control unit is operable to generate a first signal representing the presence or absence of the analytes.

32. The chemiresistor sensor probe of claim 31, further comprising a user interface in communication with said control unit, said user interface operable to receive said first signal and generate a second signal representing the presence or absence of the analytes.

33. A chemiresistor sensor system for detecting the presence of one or more analytes comprising:
   a probe including a first electrode and a second electrode each having a conductive interlocking device in direct contact with a sensor film, said probe operable to generate a first output indicative of the absence or presence of the analytes in the environment;
   a control unit in electrical communication with said first and second electrodes, said control unit operable to receive said first output from said probe and generate a signal corresponding to said first output; and
   a user interface in communication with said control unit, said user interface operable to receive said signal from said control unit and generate a second output corresponding to the absence or presence of analytes in the environment.

34. A chemiresistor sensor probe for detecting the presence of one or more target analytes comprising:
   a probe body;
   a sensor film including a crosslinked polymeric matrix mounted at an exterior surface of said probe body; and
   a first and a second terminal each having a conductive interlocking device in direct contact with said sensor film, said first and second terminals extending from said sensor film through said probe body and protruding from said probe body.

35. The chemiresistor sensor probe of claim 34, further comprising a control unit in communication with each of said first terminal and said second terminal to monitor electrical properties of said sensor film, said control unit is operable to generate a first signal representing the presence or absence of the analytes.

36. The chemiresistor sensor probe of claim 35, further comprising a user interface in communication with said control unit, said user interface operable to receive said first signal and generate a second signal representing the presence or absence of the analytes.

37. A chemiresistor sensor probe for detecting the presence of one or more analytes comprising:
   a probe body;
   a sensor film including a crosslinked polymeric matrix mounted at an exterior surface of said probe body; and
   a first terminal having a first conductive mesh plate mounted directly to said first terminal and a second terminal having a second conductive mesh plate mounted directly to said second terminal, said first and said second mesh plates each in direct contact with said sensor film.

38. The chemiresistor sensor probe of claim 37, further comprising a control unit in communication with each of said first terminal and said second terminal to monitor electrical properties of said sensor film, said control unit is operable to generate a first signal representing the presence or absence of the analytes.

39. The chemiresistor sensor probe of claim 38, further comprising a user interface in communication with said control unit, said user interface operable to receive said first signal and generate a second signal representing the presence or absence of the analytes.

* * * * *